(12) United States Patent
Yamanaka et al.

(10) Patent No.: US 9,095,890 B2
(45) Date of Patent: Aug. 4, 2015

(54) METALLIC GLASS FASTENING SCREW

(75) Inventors: Shigeru Yamanaka, Daito (JP);
Masahiro Chatani, Daito (JP);
Yasunori Saotome, Isesaki (JP); Kenji Amiya, Osaka-sayama (JP)

(73) Assignees: Maruemu Works Co., Ltd., Osaka (JP);
Tohoku University, Sendai (JP)

( * ) Notice: Subject to any disclaimer, the term of this patent is extended or adjusted under 35 U.S.C. 154(b) by 336 days.

(21) Appl. No.: 13/574,498

(22) PCT Filed: Jun. 22, 2010

(86) PCT No.: PCT/JP2010/060540
§ 371 (c)(1),
(2), (4) Date: Sep. 12, 2012

(87) PCT Pub. No.: WO2011/089742
PCT Pub. Date: Jul. 28, 2011

(65) Prior Publication Data
US 2013/0022427 A1  Jan. 24, 2013

(30) Foreign Application Priority Data

Jan. 22, 2010  (JP) ................................ 2010-011544
Mar. 23, 2010  (JP) ................................ 2010-065872

(51) Int. Cl.
*B21H 3/02* (2006.01)
*A61L 31/02* (2006.01)
(Continued)

(52) U.S. Cl.
CPC ................ *B21H 3/02* (2013.01); *A61L 31/022* (2013.01); *C22C 1/002* (2013.01); *C22C 45/00* (2013.01);
(Continued)

(58) Field of Classification Search
CPC .......... B21H 3/02; B21H 6/06; A61L 31/022; C22C 45/10; C22C 45/00; C22C 45/003; C22C 45/005; F16B 33/006; F16B 33/02; F16B 35/041

USPC .......................................................... 411/411
See application file for complete search history.

(56) References Cited

U.S. PATENT DOCUMENTS 5,217,497 A * 6/1993 Mehdian ........................ 606/268
5,288,344 A * 2/1994 Peker et al. .................... 148/403
(Continued)

FOREIGN PATENT DOCUMENTS

JP  A-2005-173558  6/2005
JP  A-2005-201789  7/2005
(Continued)

OTHER PUBLICATIONS

Jul. 27, 2010 Search Report issued in International Patent Application No. PCT/JP2010/060540 (with translation).
(Continued)

*Primary Examiner* — Gay Ann Spahn
(74) *Attorney, Agent, or Firm* — Oliff PLC

(57) ABSTRACT

A metallic glass fastening screw that is not susceptible to loosening, and is capable of implementing fastening with high strength and reliability. In processing a screw thread and a screw groove of a screw, amorphous bulk metallic glass is form-rolled at glass transition temperature or less of the bulk metallic glass serving as a member to be processed. The bulk metallic glass has a plastic strain property introduced by plastic working such as form rolling, to improve ductility. A relationship of d>0.022×D is set so that a depth from a bottom of the screw groove in the region where the plastic strain is introduced is d and an outside diameter of the screw is D, to relax stress concentration of tensile stress generated in a region at the bottom of the screw groove due to tension (axial force) applied to the screw in fastening.

11 Claims, 6 Drawing Sheets

(51) Int. Cl.

| | | |
|---|---|---|
| *C22C 45/10* | (2006.01) | |
| *F16B 33/00* | (2006.01) | |
| *F16B 33/02* | (2006.01) | |
| *C22C 1/00* | (2006.01) | |
| *C22C 45/00* | (2006.01) | |
| *B21H 3/06* | (2006.01) | |
| *F16B 35/04* | (2006.01) | |

(52) U.S. Cl.
 CPC ............ *C22C 45/003* (2013.01); *C22C 45/005* (2013.01); *C22C 45/10* (2013.01); *F16B 33/006* (2013.01); *F16B 33/02* (2013.01); *B21H 3/06* (2013.01); *F16B 35/041* (2013.01)

(56) References Cited

U.S. PATENT DOCUMENTS

| | | | | | |
|---|---|---|---|---|---|
| 5,368,659 | A | * | 11/1994 | Peker et al. | 148/403 |
| 5,482,580 | A | * | 1/1996 | Scruggs et al. | 148/528 |
| 5,618,359 | A | * | 4/1997 | Lin et al. | 148/561 |
| 5,711,363 | A | * | 1/1998 | Scruggs et al. | 164/113 |
| 5,735,975 | A | * | 4/1998 | Lin et al. | 148/403 |
| 6,007,692 | A | * | 12/1999 | Herbert et al. | 205/70 |
| 6,106,376 | A | * | 8/2000 | Rybak et al. | 451/75 |
| 6,325,868 | B1 | * | 12/2001 | Kim et al. | 148/403 |
| 6,818,078 | B2 | * | 11/2004 | Kim et al. | 148/561 |
| 6,843,594 | B1 | * | 1/2005 | Moteki et al. | 368/140 |
| 7,575,040 | B2 | * | 8/2009 | Johnson | 164/423 |
| 7,883,307 | B2 | * | 2/2011 | Pippard et al. | 411/387.1 |
| 8,961,091 | B2 | * | 2/2015 | Prest et al. | 411/424 |
| 2002/0131839 | A1 | * | 9/2002 | Kondo et al. | 411/308 |
| 2003/0034099 | A1 | * | 2/2003 | Liu | 148/561 |
| 2004/0052606 | A1 | * | 3/2004 | Kerl | 411/80.1 |
| 2007/0079907 | A1 | * | 4/2007 | Johnson et al. | 148/403 |
| 2008/0110307 | A1 | * | 5/2008 | Kong et al. | 82/124 |
| 2009/0210173 | A1 | * | 8/2009 | Arms et al. | 702/42 |
| 2010/0084052 | A1 | * | 4/2010 | Farmer et al. | 148/403 |
| 2013/0333165 | A1 | * | 12/2013 | Prest et al. | 411/439 |
| 2013/0336745 | A1 | * | 12/2013 | Trinick et al. | 411/501 |
| 2014/0007987 | A1 | * | 1/2014 | Prest et al. | 148/526 |
| 2014/0086705 | A1 | * | 3/2014 | Dawson et al. | 411/393 |
| 2014/0186138 | A1 | * | 7/2014 | Dawson et al. | 411/393 |

FOREIGN PATENT DOCUMENTS

| | | |
|---|---|---|
| JP | A-2006-002238 | 1/2006 |
| JP | A-2007-131952 | 5/2007 |
| JP | A-2008-126313 | 6/2008 |
| JP | A-2008-200734 | 9/2008 |
| JP | A-2008-238214 | 10/2008 |

OTHER PUBLICATIONS

English-language translation of Aug. 16, 2012 International Preliminary Report on Patentability issued in International Patent Application No. PCT/JP2010/060540.

Chinese Office Action issued in Chinese Patent Application No. 201080062161.3 on Mar. 5, 2014.

* cited by examiner

Fig.10
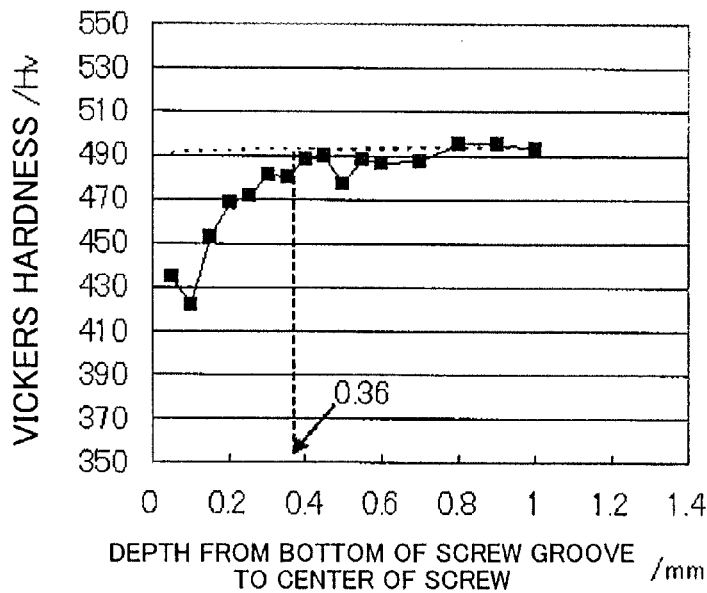
Fig.11
| | BREAKING LOAD | AREA | TENSILE BREAKING STRENGTH | ELONGATION OF SCREW |
|---|---|---|---|---|
| TYPE OF SCREW | kN | mm² | MPa | TIMES |
| COLD FORM-ROLLED METALLIC GLASS FASTENING SCREW ① | 7850 | 5.03 | 1560 | 1.8 |
| WARM FORM-ROLLED METALLIC GLASS FASTENING SCREW ② | 7825 | 5.03 | 1556 | 1.7 |
| MACHINED METALLIC GLASS FASTENING SCREW ① | 7150 | 5.03 | 1421 | 1.0 |
TENSILE SPEED: 5 mm/min.
Fig.12
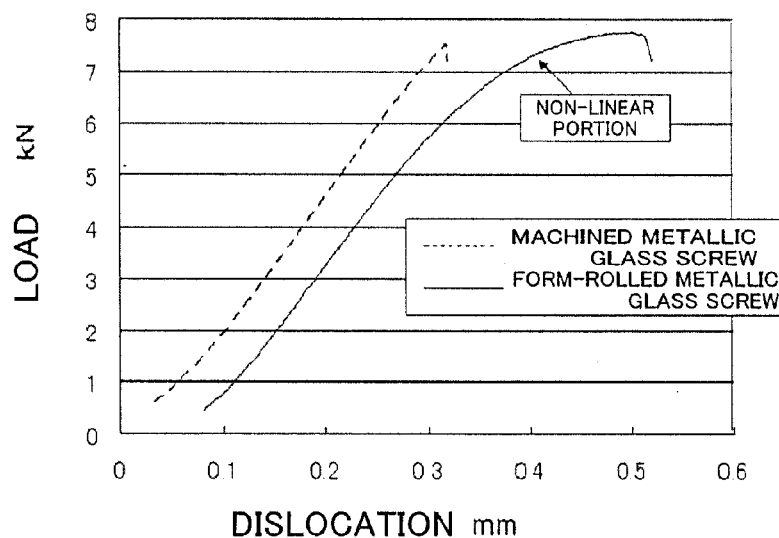

METALLIC GLASS FASTENING SCREW

TECHNICAL FIELD

The present invention relates to fastening screws characterized in a molding method and properties created by the molding method, with amorphous bulk metallic glass as being raw material.

BACKGROUND ART

Bulk metallic glass is an amorphous alloy that generally has high strength (high yield stress) and elastic limit strain (yield strain) about ten times greater than that of common metal. Its strength and modulus of elasticity (Young's modulus) can be changed by combination of constituent elements, and it can be molded into a columnar shape by casting to have a diameter equal to or smaller than a critical diameter determined by chemical components included (refer to, for example, Patent document 1). In order to apply the amorphous bulk metallic glass to small machine parts and the like, various tools, devices, methods and the like have been proposed in the casting utilizing its characteristic of small solidification shrinkage, so as to improve repletion using rotary centrifugal force and the like (refer to, for example, Patent document 2). A method is proposed in which the surface of columnar material having the bulk metallic glass on its surface is heated to glass transition temperature (Tg) or more, at which a viscous flow of the bulk metallic glass is generated, and thereafter molded by using viscous fluidity and pressing it against dies having projections and depressions (refer to, for example, Patent documents 3, 4). Also, a proposal is made in which metallic glass is flame-sprayed onto the surface of a product, so as to add the characteristic of the bulk metallic glass on the surface while keeping the characteristic of the conventional raw material inside (refer to, for example, Patent documents 5, 6).

CITATION LIST

Patent Documents

Patent document 1: Japanese Unexamined Patent Application Publication No. 2008-238214
Patent document 2: Japanese Unexamined Patent Application Publication No. 2008-126313
Patent document 3: Japanese Unexamined Patent Application Publication No. 2008-200734
Patent document 4: Japanese Unexamined Patent Application Publication No. 2005-173558
Patent document 5: Japanese Unexamined Patent Application Publication No. 2007-131952
Patent document 6: Japanese Unexamined Patent Application Publication No. 2005-201789

SUMMARY OF INVENTION

Technical Problem

A fastening screw fixes a member to be fastened while avoiding loosening by using axial force remaining after fastening and frictional force generated in a contacting bearing surface and the surface of the screw of a meshing portion of the screw. Conventionally, loosening of the screw has been avoided mainly by allowing a nut to have a special shape or special structure. If the screw itself is not susceptible to loosening, the screw can be easily removed or used repeatedly, and used in more various fields. It is possible to realize the screw that is not susceptible to loosening if its strength is increased to increase fastening force in fastening, and at the same time, if its frictional force is increased by increasing a contact area with the member to be fastened by reducing a modulus of elasticity of the screw to facilitate deformation. However, no such screw has been manufactured until now.

Bulk metallic glass is made of amorphous and generally has high strength and elastic limit strain that is about ten times greater than that of common metal, and its modulus of elasticity can be changed by combination of types of constituent elements. If the shape of the screw can be stably molded with the bulk metallic glass without any harmful defects, it is possible to manufacture a screw that is not susceptible to loosening, as compared with the conventional screws, taking advantages of the characteristics of the bulk metallic glass such as high strength, a low modulus of elasticity and high elastic limit strain. However, the bulk metallic glass is not crystalline metal, and no plastic deformation (deformation accompanying permanent strain) is caused by dislocation (a line defect that is introduced by processing and peculiar to the crystalline metal). Although various modifications have been devised, it is regarded that the bulk metallic glass basically has extremely poor ductility near ambient temperature. For processing the bulk metallic glass, casting (transferring by molten metal) is mainly used, or the bulk metallic glass is molded at glass transition temperature or more and in a supercooled liquid temperature region (generally about 400° C. plus or minus a few tens of degrees) at which a viscous flow, peculiar to the bulk metallic glass, is generated. It has been considered difficult to apply form rolling (one of processing methods using plastic deformation) of the screw to the bulk metallic glass at the glass transition temperature or less because of a particularly high working ratio and large strain gradient (difference in strain between adjacent parts) in a processed part.

Machining of the bulk metallic glass is difficult for cutting blades. When a bulk metallic glass rod or the like that is cast into a columnar shape is subjected to the machining to form a screw thread and a screw groove, the edge of the blade wears out quite easily, and stable production is very difficult. Also, loss of the material is caused, which is not preferable from an economic viewpoint.

In casting, filling of the bulk metallic glass into a portion having a sharp shape, such as the screw thread, is difficult due to the influence of surface tension and the like. A stable screw shape cannot be obtained even if pressure and rotary centrifugal force are applied thereto, and defects may be caused due to inclusion of gas generated at high temperatures. Therefore, it has been considered that the screw manufactured by the casting only is less reliable.

As the cast products are generally brittle, there has been no idea of applying the form rolling thereto to obtain a highly reliable fastening screw. Expansile material with high ductility has been used for the form rolling. Plastic working of the bulk metallic glass at ambient temperature has been considered difficult, similarly to the general cast products. Instead, the use of the viscous flow has been studied, which is generated by heating the bulk metallic glass into the supercooled liquid temperature region that is equal to or higher than the glass transition temperature. However, strict temperature management is required because its working speed is low and its processing temperature range is narrow. Also, it is necessary to provide vacuum equipment for antioxidation or the like because of high temperatures. Thus, it is difficult to perform production using this method.

In processing at a viscous flow area at the glass transition temperature or more, the viscous flow is generated from its surface to its center. Deformation is caused to the vicinity of the center to distort the shape of the cross section, and hence it is difficult to obtain the shape satisfying specifications of the screw. Thus, it is not preferable to mold the screw at the viscous flow area by the form rolling.

Attempts have been made to frame-spray metallic glass onto the surface of general metal material after being processed to have a predetermined shape, which allows only the surface to have the properties of the bulk metallic glass. However, axial force that is generated in the screw in fastening is applied over the entire cross section of the screw, and therefore, the characteristics of the bulk metallic glass, that is, high strength, a low modulus of elasticity and high elastic limit strain, are not available in the screw, unless the inside of the screw is also formed by the bulk metallic glass.

According to the form rolling applied to the common crystalline metal, high speed as an advantage in productivity is realized, and also strength is improved by using a phenomenon in which the dislocation is introduced into the processed area to cause hardening (referred to as work hardening or strain hardening). As such work hardening is not generated in the bulk metallic glass, the form rolling has not been applied thereto in order to improve mechanical characteristics.

Generally, with the screw formed by the crystalline metal with sufficient ductility, stress that concentrates in a region at the bottom of a notch-shaped screw groove when the screw is pulled in screw axis direction is relaxed due to slight plastic deformation by dislocation in that region, so that the stable fastening is realized. The fastening screw formed by the bulk metallic glass has been considered to be less reliable as the screw, because, in the case where the bulk metallic glass is formed into the fastening screw by the machining or the casting, the bulk metallic glass as the raw material has poor ductility and inadequate plastic deformation to relax stress concentration when pulled in the screw axis direction, and there is a risk of breaking by tension far weaker than the strength of the raw material.

Conventionally, the screw and general machine parts are allowed to have strength and toughness as parts mainly by hardening the surface without hardening the inside, such as carburizing that impregnates carbon with the surface, nitriding that introduces nitrogen, and the like. However, there has been no idea especially for the fastening screw of providing the ductility onto the surface to add the strength and toughness (property that is not brittle).

The fastening screw used in a living body or in contact with the outside of the living body is manufactured by the machining, which causes a problem in productivity. Although avoidance of loosening is a quite important property for the screw used for the living body, not much emphasis has been placed thereon until now.

When a member to be fastened with a low yield point and also a low modulus of elasticity, such as aluminum alloy and magnesium alloy, is fastened by a screw formed by common steel with a higher yield point and also a higher modulus of elasticity, it is likely that permanent strain (depression) is generated at a bearing surface on the side of the member to be fastened. Therefore, it is impossible to apply the large axial force and to obtain the frictional force enough to fasten the screw. Also, the similar permanent strain is generated due to external force, especially vibration, caused while in use, which gives rise to major problems including reduction in the axial force and loosening of the screw.

Therefore, it is an object of the present invention to provide a metallic glass fastening screw that is not susceptible to loosening and can be manufactured stably, while taking advantage of the properties of the bulk metallic glass, together with the steps of improving the ductility on the surface at the time of molding and adding reliability to the metallic glass fastening screw.

Solution Problem

Amorphous bulk metallic glass hardly exhibits ductility in a uniaxial tensile test at glass transition temperature or less to start a viscous flow, but exhibits slight ductility in a uniaxial compression test. Based on this fact, analysis of stress during processing by numerical analysis using a finite element method and basic experiments are carried out. As a result of this, it is found out that a plastically deformed region during the processing is under compressive stress, in form-rolling the screw having a range of a screw thread angle that is practically usable, although not all the screws. When plastic working is thus carried out under the compressive stress, opening of cracks that are generated when being deformed can be suppressed, and a considerable amount of deformation can be achieved without development of the cracks. From the repeated processing experiment and the stress analysis, it is made clear that the proper screw thread and the screw groove can be molded by the form rolling at the glass transition temperature or less without using the viscous flow.

In the bulk metallic glass, slipping is caused in a deformation band called a slip band (a deformation band at a level of a few tens of nanometers that enables plastic deformation, that is generated in a plane at which the maximum shearing stress occurs, and that is peculiar to the bulk metallic glass) so that plastic strain is generated (the plastic strain is accumulated (integrated) to cause plastic deformation). However, as this slipping is nonuniform and local, contrary to uniform deformation of common crystalline metal by dislocation, it is separated and broken when tensile force acts thereon. It should be noted that, in a region including the slip band into which the plastic strain is introduced by plastic working at the glass transition temperature or less, new slip bands originating from the slip band are easily generated, and the ductility of the region improves. If the slip band is introduced to a region where the stress is concentrated when the axial force is applied to the screw, such as a region at the bottom of the screw groove of the fastening screw, the ductility of the region is improved and the stress concentration is relaxed.

In order to solve the above problems, following means are provided.

According to an embodiment of the present invention, a metallic glass fastening screw is provided, in which amorphous bulk metallic glass is molded by form rolling at glass transition temperature or less of the bulk metallic glass serving as a member to be processed, in processing a screw thread and a screw groove of a screw.

The bulk metallic glass has the property that plastic strain is introduced in a region including a slip band by plastic working such as the form rolling, so as to improve ductility. By effectively using this property, the embodiment of the present invention provides the metallic glass fastening screw in which a relationship of $d > 0.022 \times D$ holds provided that a depth from a bottom of the screw groove in a region where plastic strain is introduced by the form rolling is d and an outside diameter of the screw is D, in order to relax stress concentration of tensile stress generated in a bottom region of the screw groove by tension (axial force) applied to the screw in fastening.

The embodiment of the present invention provides the metallic glass fastening screw in which the screw comprises a triangular-threaded screw whose screw thread angle is within a range of 40 to 70 degrees.

The embodiment of the present invention provides the metallic glass fastening screw in which the bulk metallic glass is used for a living body by including at least one of Ti-base, Pd-base and Zr-base.

The embodiment of the present invention provides the metallic glass fastening screw in which, when fastening is made into a member to be fastened with a low yield point and a low modulus of elasticity, the bulk metallic glass includes any one of Mg-base, Pt-base, Ti-base and Zr-base having a modulus of elasticity equal to or lower than that of the member to be fastened in order to avoid loosening due to permanent strain (depression) of the member to be fastened in fastening.

According to an embodiment of the present invention, a manufacturing method of a metallic glass fastening screw is provided, in which the metallic glass fastening screw is molded by form rolling with mean stress of a plastically deformed region of bulk metallic glass being compressive stress or tensile stress of one-third or less of tensile breaking strength of the bulk metallic glass.

Advantageous Effects of the Invention

According to the present invention, a fastening screw that is not susceptible to loosening is provided by allowing the screw to have high strength, a low modulus of elasticity and high elastic limit strain that are the common properties of amorphous bulk metallic glass. The object of the present invention is to provide a manufacturing process of a metallic glass fastening screw capable of improving strength, toughness (property that is not brittle) and reliability of the fastening screw, and also the metallic glass fastening screw having stable quality and productivity, having improved ductility near the surface of the screw to relax stress concentration generated near a screw groove of the screw, and keeping strength of the bulk metallic glass as it is in its inside, by being form-rolled at ambient temperature and at relatively low temperature higher than the ambient temperature but equal to or lower than glass transition temperature.

The details of the effects of the invention will be explained.

The bulk metallic glass includes the properties that no other common metal includes, that is, high strength, a low modulus of elasticity and high elastic limit strain. When it is applied to the fastening screw, it is possible to minimize a change in axial force due to strain of a member to be fastened. Even when, for example, the member to be fastened is subjected to compressive deformation by external force or vibration, reduction in the axial force can be minimized, which makes it possible to realize a screw that has stable axial force and is not susceptible to loosening, as compared with a steel screw with a high modulus of elasticity.

Lightweight metal material generally has a low yield point and a low modulus of elasticity. When it is fastened by a conventional steel screw with a high modulus of elasticity, deformation (depression) is caused at a bearing surface on the side of the member to be fastened, to cause loosening. When the bulk metallic glass having a modulus of elasticity equal to or lower than that of the member to be fastened is selected, and the metallic glass fastening screw manufactured according to the present invention is used, the bearing surface on the screw side is deformed together with the member to be fastened. A contact area at the bearing surface is increased, bearing stress is reduced, depression is suppressed, and frictional force is increased, so that the fastening that is not susceptible to loosening can be realized.

Meanwhile, ceramic, which is also the lightweight material, has high compressive strength and also a high modulus of elasticity. When it is fastened by the metallic glass fastening screw, the screw is fastened therein tightly taking advantage of its characteristic of high strength. Then, the metallic glass fastening screw itself is deformed, the contact area of the bearing surface and a meshing portion of the screw is increased, and the frictional force is increased, so that the fastening that is not susceptible to loosening can be realized.

When the bulk metallic glass is form-rolled at the glass transition temperature or less, plastic strain is introduced near the surface, and slip bands are concentrated in a screw thread and a screw groove, so as to improve ductility at these regions. The ductility created by the form rolling relaxes the stress concentration at a bottom region of the screw groove caused by the axial force (tension) of the screw generated in fastening.

Thus, the surface of the screw is added with the ductility, and the inside is allowed to have high strength of the bulk metallic glass as it is. Thereby, it is possible to suppress brittle fracture caused by cracks from the surface attributable to its shape, reduce variations in strength, and realize highly reliable, well-balanced screws with high strength.

According to the form rolling, loss of the material, as is generally caused in plastic working, can be reduced. Also, microscopic defects that are introduced by casting are mechanically crushed (forging effect), to let a part of the defects near the surface diminish. Thus, it is possible to manufacture highly-reliable screws.

Some bulk metallic glass have combinations of components that has corrosion resistance and biocompatibility (causing no rejection reaction by a living body even when included in the living body), other than general mechanical characteristics. By selecting the components suited to such environment, it is possible to realize fastening that is not susceptible to loosening in various application fields.

The screws applied herein include not only the common fastening screws having a screw head but also general screws used by applying the axial force to a threaded portion.

BRIEF DESCRIPTION OF THE DRAWINGS

FIG. 10 shows an indentation test by a Vickers indenter;

FIG. 11 shows a tensile breaking strength test of the screw;

FIG. 12 is a load-displacement diagram; and

DESCRIPTION OF EMBODIMENTS

A manufacturing method of a screw according to an embodiment of the present invention will be explained with reference to FIG. 1 to FIG. 5, and its test results will be shown in FIG. 6 to FIG. 13.

Bulk metallic glass as raw material includes the common properties of high strength, a low modulus of elasticity, and high elastic limit strain, which are advantageous for fastening screws not susceptible to loosening. Also, as its physical/chemical property changes according to its components of alloy, a metallic glass fastening screw can be manufactured by selecting the components of alloy for the bulk metallic glass (metal to be a main component is referred to as a base of the bulk metallic glass) suited to a member to be fastened, fastening conditions and environment.

When the screw is fastened in a member to be fastened with a low yield point and a low modulus of elasticity, such as aluminum alloy and magnesium alloy, Mg-based, Pt-based, Ti-based, or Zr-based bulk metallic glass or the like, having the similar or lower modulus of elasticity, is selected as the raw material of the fastening screw in order to avoid loosening due to permanent strain (depression) of the member to be fastened. Thus, deformation on the screw side is increased to increase a contact area at a bearing surface, so that the depression is prevented by reducing bearing stress, and frictional force is increased to avoid loosening. For the member to be fastened with a high modulus of elasticity and high compressive strength, such as ceramic, the bulk metallic glass with high strength and a relatively low modulus of elasticity may be used to avoid loosening, by increasing fastening force and increasing frictional force by increasing a contact area at a bearing surface and a meshing portion of the screw.

When the screw is fastened in an area where corrosion resistance, as well as avoidance of loosening, is required, the bulk metallic glass with high corrosion resistance, such as Ni—Cr-base, is applied.

When used in a living body, Ti-base, Pd-base or Zr—Pd-base or the like is applied so as to realize the fastening screw that has biological compatibility with less allergy or rejection reaction in the living body and is not susceptible to loosening.

Figure 1:
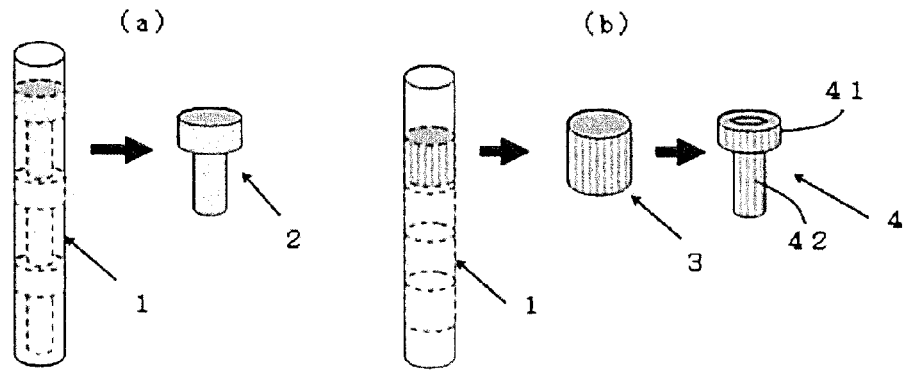
FIG. 1(a) and FIG. 1(b) are views showing formation of an intermediate product before form rolling.

FIG. 1 show a method of forming the bulk metallic glass into an intermediate product before being form-rolled into a screw. The bulk metallic glass can be cast into a columnar shape after its component element is heated to a melting point or more and melted by arc melting and the like. By machining a bulk metallic glass round bar 1 cast into the columnar shape as shown in FIG. 1(a), it is possible to form an intermediate product before form rolling, as a machined intermediate-shaped product 2 of the screw as shown in FIG. 1(a). However, the machining of the bulk metallic glass is not easy, a loss is caused by the machining, and, when hole drilling in a head is necessary for a hexagon socket screw and the like, the drilling is difficult. In view of these circumstances, it is more preferable to cut the bulk metallic glass round bar 1 into pieces each having a volume corresponding to that of a desired screw, as material for casting 3 shown in FIG. 1(b), which is remelted in an oxygen free atmosphere, cast into a mold having a screw head 41 and a screw axis 42, to be molded into the intermediate product before the form rolling, such as a cast intermediate-shaped product 4 of the screw, as shown in FIG. 1(b).

Figure 2:
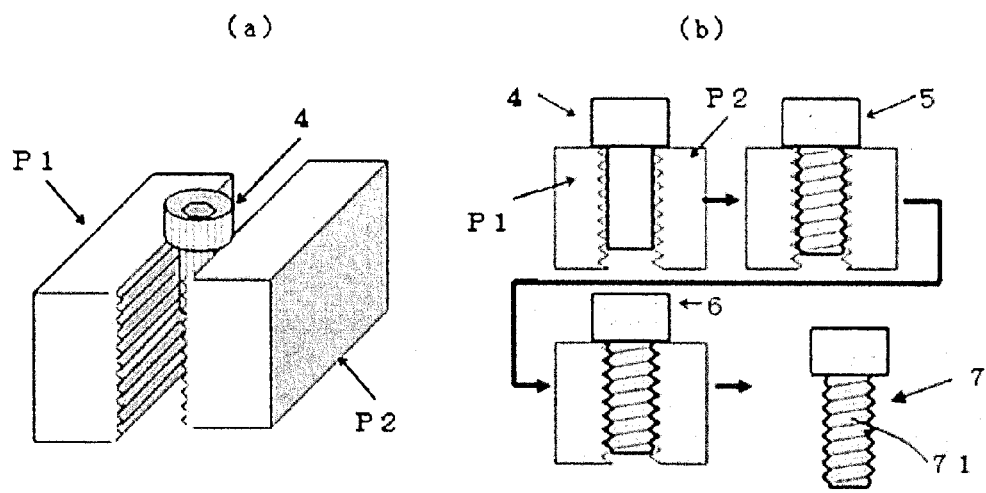
FIG. 2(a) and FIG. 2(b) are views showing the form rolling.

FIG. 2 show how the form rolling is performed. FIG. 2(a) shows the form rolling in which the cast intermediate-shaped product 4 of the screw is disposed between two dies (rolling die movement side P1 and rolling die fixture side P2) having a screw thread shape and a screw groove shape, and a screw axis 42 is rolled therebetween while being pressed against the dies. FIG. 2(b) shows the form rolling in which die shapes are gradually transferred to the cast intermediate-shaped product 4 of the screw, as in the initial stage 5 of the form rolling and in the middle stage 6 of the form rolling, so as to mold a form-rolled screw 7.

The reason why the form rolling of the bulk metallic glass is possible at its glass transition temperature or less will be explained. First, terms used herein will be explained. Mean stress, also referred to as mean normal stress, is a mean value of normal stress generated at vertical planes at a point, and shows if the point is in a compressional state (negative value) or in a tensile state (positive value). Equivalent stress is a value relating to shearing stress generated in a direction parallel to a plane, and is made to correspond to tensile stress of a simple round bar (referred to uniaxial tension or simple tension) in order to simplify the state of multi-axis stress that is generally nonuniform. Meanwhile, equivalent strain shows the state of generally nonuniform strain that is made to correspond to strain of the uniaxial tension. Further, tensile breaking strength is a tensile breaking load converted into a value per unit area by being divided by a cross-sectional area, and uses the same unit as the stress.

In a uniaxial tensile test, the bulk metallic glass hardly exhibits ductility at ambient temperature. In order to mold the bulk metallic glass at the glass transition temperature or less, therefore, the molding should be performed while the mean stress in a region deformed by receiving force from the dies is negative (that is, in the compressional state). This is because development of cracks that cause breakdown can be avoided in the compressional state. In the uniaxial tension, deformation is made without breakdown until just before it breaks, and therefore it is possible to include the mean stress just before the breaking in the uniaxial tension, that is, tol one-third of the tensile breaking strength. (This shows the mean stress in the maximum tensile load state just before the breaking in the uniaxial tension. In the uniaxial tension, the stress in two directions vertical to a tension axis is zero, and hence one-third of the stress in the tension axis direction becomes the mean stress.) In order to mold the bulk metallic glass at the glass transition temperature or less, the mean stress needs to be one-third of the tensile breaking strength of the bulk metallic glass or less, including the range where the mean stress is negative.

Effectiveness of the above necessary conditions has not made clear sufficiently thus far, in the processing of the bulk metallic glass by the form rolling and the like, in which large plastic strain concentrates on the vicinity of the surface to increase a strain gradient. After repeating stress analysis by a finite element method and a processing experiment, the effectiveness is made clear in triangular-threaded screws and other metallic glass fastening screws.

Figure 3:
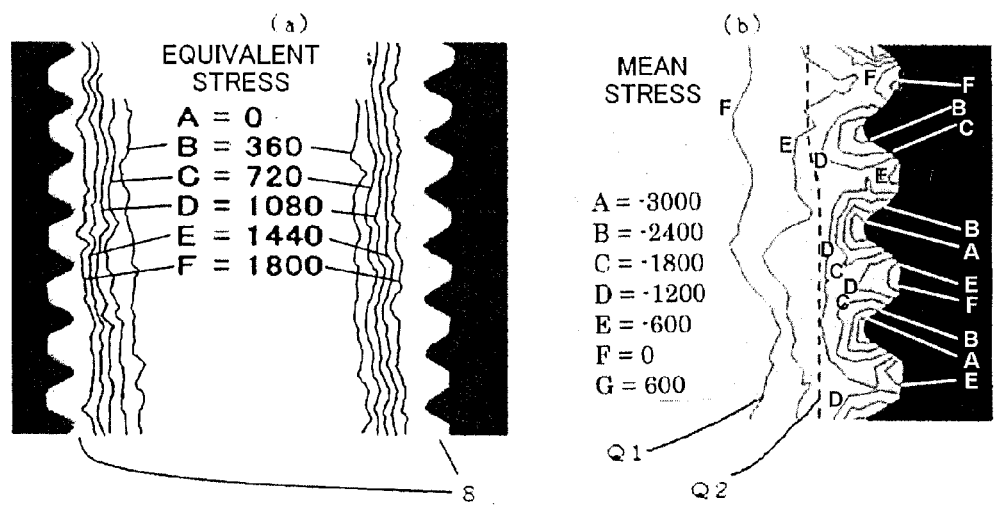
FIG. 3(a) and FIG. 3(b) are views showing stress distribution in a cross section of a screw.

FIG. 3 show stress distribution in the cross section of the screw during the form rolling, calculated by the finite element analysis. The details will be explained together with FIG. 2 showing the form rolling. According to the form rolling, as shown in FIGS. 2(a) and 2(b), the screw axis 42 is rolled while being pressed against the two dies of the rolling die movement side P1 and the rolling die fixture side P2, each having the shape corresponding to the screw thread and the screw groove, and the die patterns are transferred thereto to mold the screw thread and the screw groove. In the stress analysis of this process, a rigid-perfectly plastic solid model (a model with the assumption that the equivalent stress to start the plastic deformation has a fixed value), without work hardening, is adopted, in view of the properties of the bulk metallic glass. Here, 1800 MPa, as an experimental value of Zr-based metallic glass, is regarded as the equivalent stress to start the plastic deformation and as the fixed value. According to the analysis by the finite element method as one of numerical analyses, equivalent stress distribution showing a region with the plastic strain generated inside the screw, in the middle of the form rolling represented by the middle stage 6 of the form rolling in FIG. 2(b) showing the form rolling, is as shown in FIG. 3(a) showing the equivalent stress distribution of the screw during the form rolling. This makes it clear that a plastically deformed region is near the screw thread and the screw groove, and in a region 8 marked with diagonal lines, with the equivalent stress of 1800 MPa or more (MPa is the unit of the stress) shown by an outline F in the drawing. Meanwhile, mean stress distribution at the same processing timing is shown in FIG. 3(b) showing the mean stress distribution of the cross section of the screw. This makes it clear that the mean stress is negative and under the compressive stress in the most part on the side of the screw thread and the screw groove (right side in the drawing) from an outline Q1 where the mean stress is 0 MPa, and that an outline Q2, that shows a boundary of the plastically deformed region and has the equivalent stress of 1800 MPa, is also included therein. In FIG. 3(b), some regions that are near the tip end of the screw thread and are not in contact with the die have the positive mean stress slightly exceeding 0 MPa at the same processing timing. However, it is clear that the mean stress is 600 MPa or less, which is one-third of the tensile breaking strength of the bulk metallic glass (1800 MPa). Thus, it is theoretically proven that the form rolling has the effect of preventing the breakdown due to the development of the cracks.

The above theoretical contents are properly-validated by a plurality of experiments. The form rolling employs typical sequential working, that is, the columnar bulk metallic glass is rolled while being pressed against the dies for about five times with the amount of pressing gradually increased and repeatedly added to obtain the finished product with the screw groove of the dies being transferred thereto. As the form rolling makes progress, slip bands are concentrated with the plastic strain being introduced therein, ductility of the bulk metallic glass is improved, and deformation capability is improved, which may be one of the reasons why the screw can be molded at the glass transition temperature or less.

The screw thread and the screw groove of the screw receive force from the dies during the form rolling. The shape of the screw determines the state of the stress generated in the bulk metallic glass as the material to be processed during the form rolling, that is, whether the mean stress during the processing is negative (compression) or positive (tension).

Figure 4:
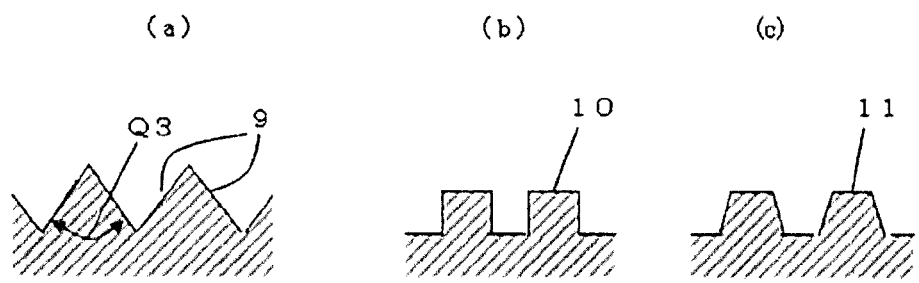
FIG. 4(a), FIG. 4(b) and FIG. 4(c) show cross sections of screw threads.

FIG. 4 show cross sections of the screw threads. It is made clear by the above-described finite element analysis that, in a screw thread 9 of a triangular-threaded screw generally used for fastening, as shown in FIG. 4(a), the mean stress of the entire plastically deformed region is the compressive stress or one-third or less of the tensile breaking strength at any time from the start to the end of the form rolling. Thus, it is made clear and validated by the experiments that the form rolling of the metallic glass fastening screw, including the triangular-threaded screw such as a metric screw thread and a unified screw thread, is theoretically possible.

On the contrary, in a square-threaded screw shown in FIG. 4(b) and a trapezoidal-threaded screw shown in FIG. 4(c), high tensile stress exceeding one-third of the tensile breaking strength is generated near plastically deformed regions, that is, a screw thread 10 of the square-threaded screw and a screw thread 11 of the trapezoidal-threaded screw. Therefore, it is generally difficult to perform stable and normal processing without development of cracks at the glass transition temperature or less, which is confirmed by the experiments and the finite element analysis, It should be noted that the normal processing is possible if the shapes are changed so that the mean stress becomes the compressive stress or one-third or less of the tensile breaking strength in the region having the equivalent stress exceeding the value to start the plastic deformation (corresponding to the region 9 where the equivalent stress is 1800 MPa or more in the above-described example).

Regarding a screw thread angle Q3 of the triangular-threaded screw as in FIG. 4(a) showing the cross section of the screw thread, the axial force cannot be maintained sufficiently when it is 40 degrees or less, and the frictional force at a meshing portion of the screw is reduced to facilitate loosening when it is 70 degrees or more. Therefore, the screw thread angle needs to be within the range of 40 to 70 degrees in order to maximize the function of the fastening screw. The finite element analysis and the experiments respectively show that, with the screw having such a screw thread angle, the mean stress in the region where the plastic deformation is caused due to the plastic strain during the form rolling is either the compressive stress or one-third or less of the tensile breaking strength, so that the form rolling of the bulk metallic glass can be realized at the glass transition temperature or less.

Next, mechanical characteristics of the metallic glass fastening screw thus manufactured by the form rolling at the glass transition temperature or less will be explained.

When the screw having the screw groove is fastened, tension (axial force) acts on the screw and high stress is generated near the screw groove due to the shape of the groove (this is caused because the screw groove is in a V-shape and closely resembles a notch-shape). The highest stress develops near the bottom of the first screw groove on the side of the screw near a nut bearing surface, because this is also a fitting portion to a nut. The tension by bending effect of the screw thread, not only the tension of the screw as a whole, is superimposed thereon (for example, Yamamoto, Akira et al, Neji Shimetsuke Kikou Sekkei No Pointo, Japanese Standards Association, p. 190 etc.). Accordingly, a screw formed by brittle material with poor ductility is broken near the bottom of the first screw groove on the side of the screw near the nut bearing surface, and therefore it is difficult to realize reliable fastening.

Figure 5:
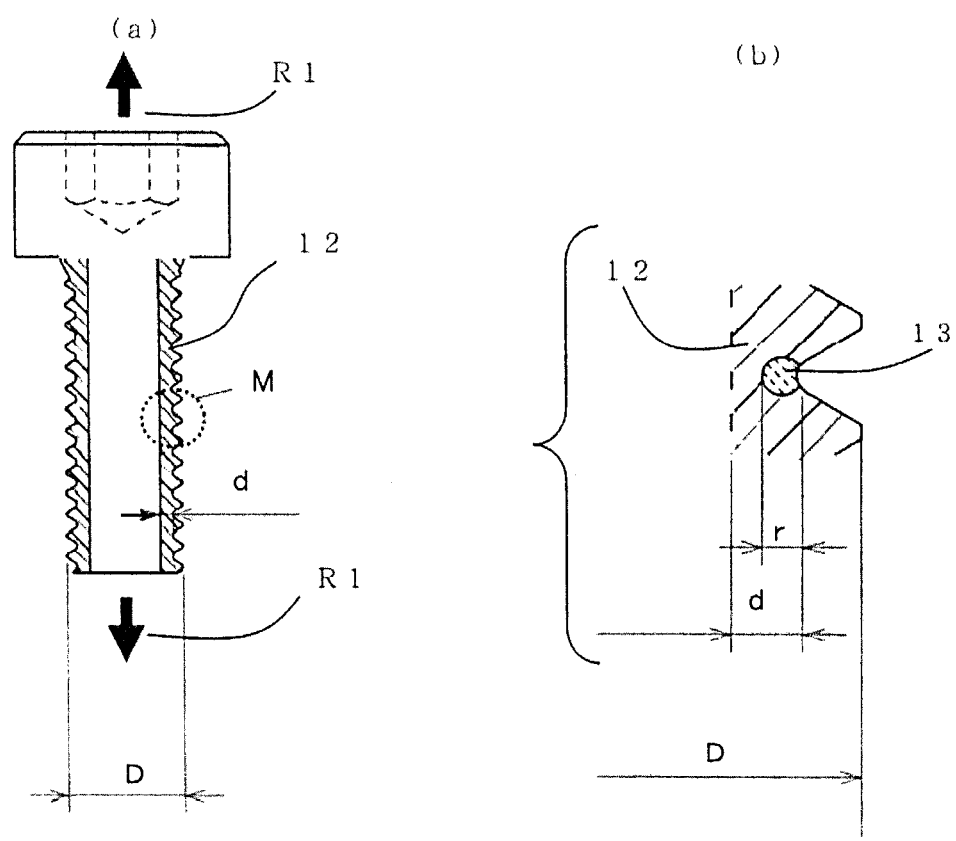
FIG. 5(a) and FIG. 5(b) are cross sectional views of the screw.

FIG. 5 show the cross section of the screw made by the form rolling. In FIG. 5(a), a region where the plastic strain is introduced by the form rolling, that is, a region 12 including the slip band that is peculiar to the bulk metallic glass is marked with diagonal lines. The bottom of the screw groove (region near the bottom) in which the high tensile stress develops when the tension (axial force) acts on the screw by being fastened is also included in the region 12 including the slip band.

The effect of the ductility at the bottom of the screw groove will be explained from a theoretical point of view.

According to fracture mechanics, extremely high tensile stress develops at an end of the crack developing to the direction vertical to the tensile load applied. When the end region has the ductility, the portion is subjected to tensile plastic deformation to relax the tensile stress. The screw has the screw groove whose shape is similar to the notch, and the screw groove acts as the end from which the crack develops when the tensile load by the axial force is applied in tensile direction R1 shown in FIG. 5 showing the cross section of the screw, so that the high tensile stress is generated. When the bottom region of the screw groove has the ductility, a tensile plastic deformation region 13, as shown in FIG. 5(b) enlarging an area M in FIG. 5(a), is subjected to the tensile plastic deformation to relax the tensile stress. A calculation method for obtaining the size of the tensile plastic deformation region 13 will be explained by using FIG. 5. As in the enlarged view of the screw groove shown in FIG. 5(b), supposing that a depth (distance) from the bottom of the screw groove in the tensile plastic deformation region 13 was r as in FIG. 5(b), r applied with the tensile load to an elastic limit can be approximately calculated according to the fracture mechanics, by using a critical stress intensity factor Kc (described later), an elastic limit stress σ1 (value obtained by dividing an elastic limit tensile load by an effective sectional area) and a circular constant π as follows:

Expression 1

$$r = (Kc)^2/(\pi \times (\sigma 1)^2) \quad (1)$$

It should be noted that this Kc can be obtained as follows by the shape of an area where the crack develops and the elastic limit stress σ1. Supposing that the screw groove was a crack and the screw was an infinite round bar having an annular crack at regular intervals, the critical stress intensity factor Kc can be calculated as expression (2) using an outside diameter D of the screw in FIG. 5(b). (Refer to Usami. Kikai Sekkei, volume 51, no. 15 (2007), and Nishitani et al. Transactions of the Japan Society of Mechanical Engineers, Series A, vol. 50, no. 453 (1984).) Some of the theses argue that a modulus should be 0.30 for safety, but a standard value of 0.26 is used as the modulus in the expression (2).

Expression 2

$$Kc = 0.26 \times \sigma 1 \times D^{1/2} \quad (2)$$

Where, the expression (2) is substituted into the expression (1) as follows:

$$r = 0.022 \times D \quad (3)$$

It is necessary for the position of the depth r of the tensile plastic deformation region 13 of the screw groove to be included in the region where the plastic strain is introduced by the form rolling and the slip bands concentrate, and to have the improved ductility. Specifically, when the depth of the region where the plastic strain is introduced by the form rolling is supposed to be d, d needs to be larger than r, that is:

$$d > r \quad (4)$$

That is, from the expression (3) and the expression (4), it needs to be as follows:

$$d > 0.022 \times D \quad (5)$$

In order to obtain the stable effect, it is desirable that the depth d of the region 12 including the slip band, into which the plastic strain is introduced by the form rolling, is 1.5 or more times greater than this minimum value, in consideration of variations and the like.

When the screw is formed by casting or machining the shape before the form rolling to form an intermediate shape having a part of the screw thread and the screw groove, and then subjecting the intermediate shape to the form rolling, the size of the region into which the plastic strain is introduced by the form rolling may be inadequate and the conditions of the expression (4) may not be satisfied. At this time, it is impossible to obtain the sufficient effect of relaxing the stress concentration even after the form rolling.

When the form rolling is performed at the glass transition temperature or less, the inside, in which the plastic strain is not caused, has high strength because it is the bulk metallic glass as being cast. The plastic strain is introduced by the form rolling, the slip bands concentrate near the surface, and the ductility is improved, as in the region 12 including the slip band shown in FIG. 5. This unprecedented new structure and design of the screw can relax the stress concentration due to the shape of the screw groove, prevent the development of the crack, improve the breaking strength of the screw, and give stability to the strength, as compared with the metallic glass fastening screws without the form rolling.

The glass transition temperature is generally 300° C. or more, though variations may be caused by the type of the bulk metallic glass. A temperature range according to this invention is set to be equal to or lower than the glass transition temperature, but, in taking productivity into consideration, the temperature equal to or lower than 200° C. is preferable because the needs for strict heat management, special lubricant oil, and a device for antioxidation can be eliminated.

A working speed is set in consideration of prevention of surface seizing with the dies, and crystallization of the bulk metallic glass due to temperature rising. When the working speed is too high, for example, the area to be processed falls into an adiabatic state. Then its temperature rises, crystallization is caused in the area, and the area may become brittle, even when the temperature is equal to or lower than the glass transition temperature. Therefore, it is preferable to limit a strain rate to be 100 s$^{-1}$ or less.

As to the form-rolled metallic glass fastening screw, it is possible to obtain an amorphous material ratio by analyzing its microscopic structure of the form-rolled screw thread and the screw groove by an X-ray diffraction method (XRD). Existence of macro segregation and crystallized particles of several hundred microns or more, which causes embrittlement, may be harmful and not accepted, but smaller crystal particles, including fine particles or nanoparticles, may be accepted if not harmful. In order for the metallic glass to function as the fastening screw, it is preferable that 50% or more of the form-rolled screw axis 71 is amorphous. It should be noted that the screw head 41 may have the lower percentage because it hardly contributes to the axial force.

DESCRIPTION OF EMBODIMENT

An embodiment of the present invention will be explained.

A fastening screw to be manufactured is a hexagon socket head cap screw with a thread angle of 60 degrees and a size of M3 specified by JIS, which is also a full thread (a screw having a screw thread and a screw groove over its entire axis) having a length beneath its neck of 8 mm.

Zr-based bulk metallic glass Zr55Al10Cu30Ni5 (numbers show ratios of components) with high strength, high glass forming ability, and a high impact resistance value is employed as bulk metallic glass. Glass transition temperature of this bulk metallic glass is 410° C.

Fe-base followed by Ni-base are preferable from a strength viewpoint, but the Fe-base is brittle and the Ni-base has a small critical diameter (maximum diameter with which the bulk metallic glass becomes amorphous when being cast) and is easily crystallized, which are not preferable. On the contrary, the Zr-base has the high glass forming ability and tensile breaking strength of 1800 MPa, which is sufficiently high for the screws. It also has a large elastic region, including a modulus of elasticity of 90 GPa (90000 MPa) and yield strain of 2.0%. Thus, it is possible to realize fastening into a member to be fastened made from a wide variety of materials including light metal having a low modulus of elasticity and ceramic having a high modulus of elasticity, while avoiding loosening.

As shown in FIG. 1, raw material is cast into a round bar 1 of the bulk metallic glass having a diameter of 5.25 mm and a length of 200 mm, which is cut into pieces each having a volume corresponding to that of the target screw, to form material for casting 3.

In an atmosphere in which the air is vacuumed and replaced with an argon gas, the material for casting 3 is remelted by raising the temperature to 920° C. by high frequency induction heating, flowed into a mold for forming a screw head 41 and a screw axis 42, to form a cast intermediate-shaped product 4 for the screw. Steel having appropriate thermal conductivity and a mold life is selected for the mold, in consideration of a critical cooling rate that is a minimum cooling rate for the bulk metallic glass to become amorphous.

The cast intermediate-shaped product 4 for the screw, having the size of M3, is form-rolled as shown in FIG. 2 under two conditions of ambient temperature (about 20° C.) and warm temperature (about 180° C.), using a rolling die movement side P1 and a rolling die fixture side P2 having a screw thread angle of 60 degrees, so as to mold the screw thread and the screw groove.

Figure 6:
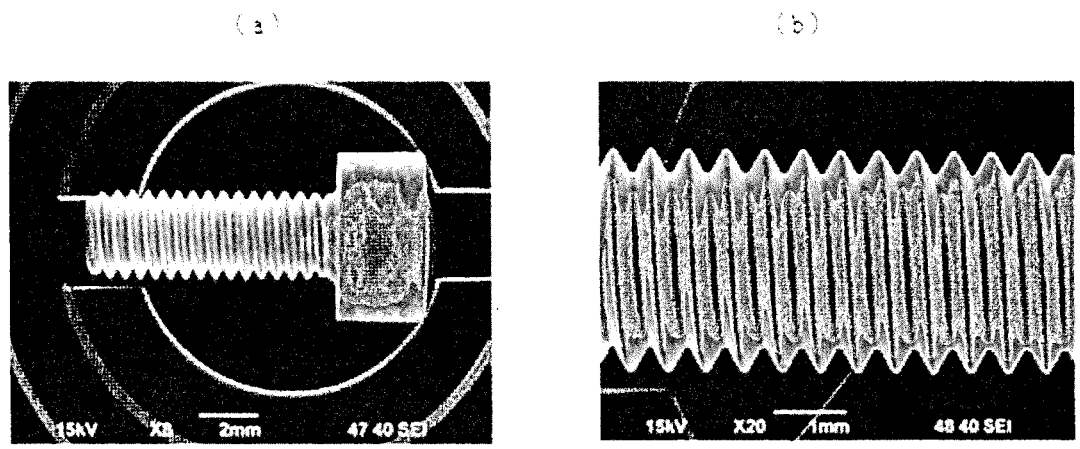
FIG. 6(a) and FIG. 6(b) show an external view of the screw.

FIG. 6 are scanning electron microscope images showing an external view of a screw 7 after the form rolling at the ambient temperature. FIG. 6(a) shows the whole image, and FIG. 6(b) is an enlarged image of the screw. Thus, it is confirmed that a form-rolled screw thread 14 is molded properly. By dimensional measurement of the respective parts, it is also confirmed that the form-rolled screw 7 is within specifications.

Figure 7:
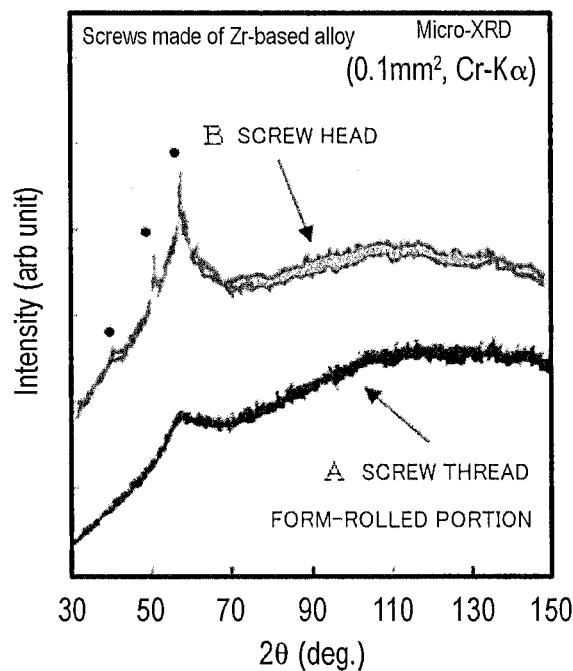
FIG. 7 shows results of an X-ray diffraction test.

Results of an X-ray diffraction test (XRD) using a Cr—Kα X-ray are shown in FIG. 7. A vertical axis shows intensity of the X-ray and a horizontal axis shows an incident angle, and test results at the screw thread and the screw head are shown as A and B, respectively. As no clear peak, showing existence of crystals, exists in diffracted intensity at the form-rolled screw thread as A, it is confirmed that A is amorphous. On the contrary, some peaks exist at the screw head as B, and it is confirmed that B is partially crystallized.

Figure 8:
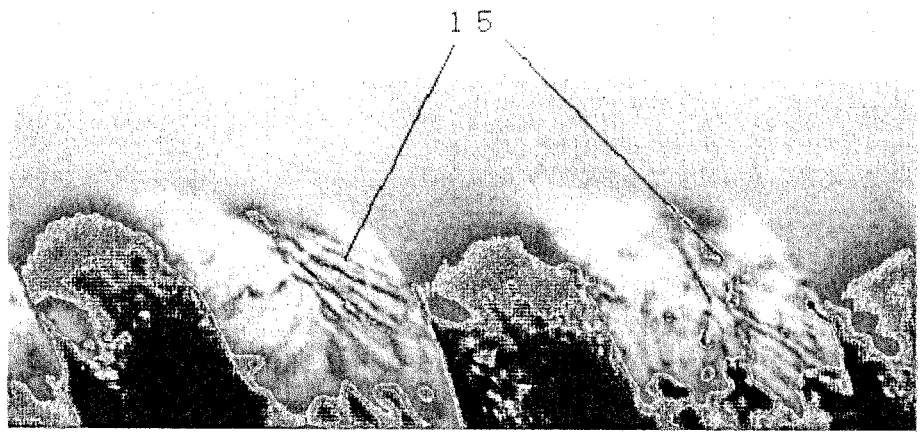
FIG. 8 shows the screw thread during the form rolling.

FIG. 8 shows the screw thread during the form rolling. Stripe-shaped slip bands 15 can be found in regions where the two screw threads are being formed. As the form rolling proceeds, the slip bands concentrate near the screw thread and the screw groove to improve the ductility at these regions.

Figure 9:
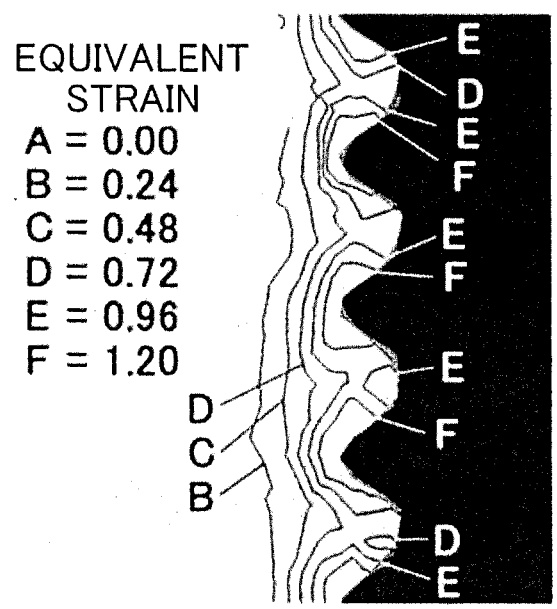
FIG. 9 shows equivalent strain distribution of a cross section of the screw.

FIG. 9 shows equivalent strain distribution in a cross section of the screw. It is possible to use this to theoretically obtain a depth d of a region 12 including the slip band into which the plastic strain is introduced by the form rolling, as shown in FIG. 5. (It can be obtained by the outline Q2 where the equivalent stress is 1800 MPa in FIG. 3, but the equivalent strain distribution is used here for simplicity's sake.) Specifically, a region from an outline B to the side of the surface of the screw in FIG. 9 has the equivalent strain of 0.24 or more. As it exceeds elastic limit strain of the target bulk metallic glass, that is 0.02, it is made clear that the plastic strain is introduced in the region. As the depth of the outline B from the screw groove is about 0.3 mm, the depth d of the region 12 including the slip band into which the plastic strain is introduced should be deeper than at least 0.3 mm and its value should be greater than 0.3 mm. Next, when the tensile load shown in FIG. 5 is applied in the tensile direction R to around its breaking load, the depth r of the tensile plastic deformation part 13 formed at the screw groove becomes r=0.022×3 mm=0.066 mm from the expression (3), as the outside diameter D of the targeted M3 screw is 3 mm. Thus, d is four times or more greater than r, and therefore d>r of the expression (4), that is, the relationship of d>0.022D of the expression (5) holds. Thus, the tensile plastic deformation part 13 that is formed when the tensile load is applied is included in the region 12 including the slip band that is introduced by the form rolling and that gives ductility, so that the tensile stress generated at the bottom of the screw groove can be relaxed.

FIG. 10 shows results of a Vickers hardness test of the cross section of the screw. A vertical axis shows Vickers hardness with a load of 100 g, and a horizontal axis shows a depth from the bottom of the screw groove toward the center of the screw axis in the vertical section of the screw. Measurement is carried out at intervals of 0.05 mm to make a line graph as in FIG. 10. In FIG. 10, the hardness is reducing from the point where the depth from the groove bottom is 0.36 mm toward the surface, and hence it is possible to regard this point as the depth d of the region 12 including the slip band, in which the plastic strain is introduced by the form rolling. This value is almost the same as the analysis result of the equivalent strain by the above-described finite element method, and it is clear from these results that the relationship of d>0.022D holds.

FIG. 11 shows results of a tensile breaking strength test of the form-rolled screw 7 using the bulk metallic glass, and a machined metallic glass fastening screw whose screw thread and screw groove are formed by subjecting the cast intermediate shape 4 of the screw to the machining, both of which have the same size of M3. The tensile breaking strength of the screw is shown by a value obtained by dividing the maximum tensile breaking load by an effective sectional area of the screw (an area of a circle having a diameter of (a pitch diameter of the screw+a diameter of the screw groove)/2). Both of a cold form-rolled product that is form-rolled at ambient temperature and a warm form-rolled product that is form-rolled at warm temperature (180° C.) have the tensile breaking strength greater than that of the machined metallic glass fastening screw that is formed by the machining. Elongation of the screw (an amount of change in the length from beneath the neck of the screw to the nut bearing surface until it breaks by tension) is shown by scaling assuming that average elongation of the machined metallic glass fastening screw is 1.0. Both of the cold form-rolled and warm form-rolled metallic glass fastening screws have the elongation values 1.7 to 1.8 greater than that of the machined metallic glass fastening screw.

FIG. 12 is a load-displacement diagram of a tensile test of the metallic glass fastening screw form-rolled at ambient temperature and the machined metallic glass fastening screw. With a horizontal axis showing displacement in tensile direction showing the elongation of the screw and a vertical axis showing a load, the diagram shows relationships when the screws are pulled until they are broken. The machined metallic glass fastening screw, shown by a broken line, is suddenly broken in the middle of the straight line without exhibiting the ductility because it does not include the region 12 including the slip band caused by the form rolling, as in FIG. 5. On the contrary, the form-rolled metallic glass fastening screw slightly deviates from linearity in the middle and presents a non-linear curve that is projected upward, as the displacement increases. This is because tensile plastic elongation is caused at the tensile plastic deformation part 13 in FIG. 5(b) in the bottom of the screw groove, meaning that the ductility as the screw is represented.

In FIG. 12, a breaking load of the form-rolled metallic glass fastening screw is greater than that of the machined metallic glass fastening screw. In the form-rolled metallic glass fastening screw, the stress concentration in the screw groove is relaxed and therefore, it does not suddenly broken in the middle of the straight line, that is, in the middle of the elastic region, such as in the case of the machined screw and the brittle material. The inside of the screw maintains the strength of the bulk metallic glass as being cast, and the region 12, including the slip band into which the plastic strain is introduced by the form rolling, is disposed near the screw thread and the screw groove so as to add the ductility to this region, both of which are well balanced to improve the breaking strength.

Figure 13:
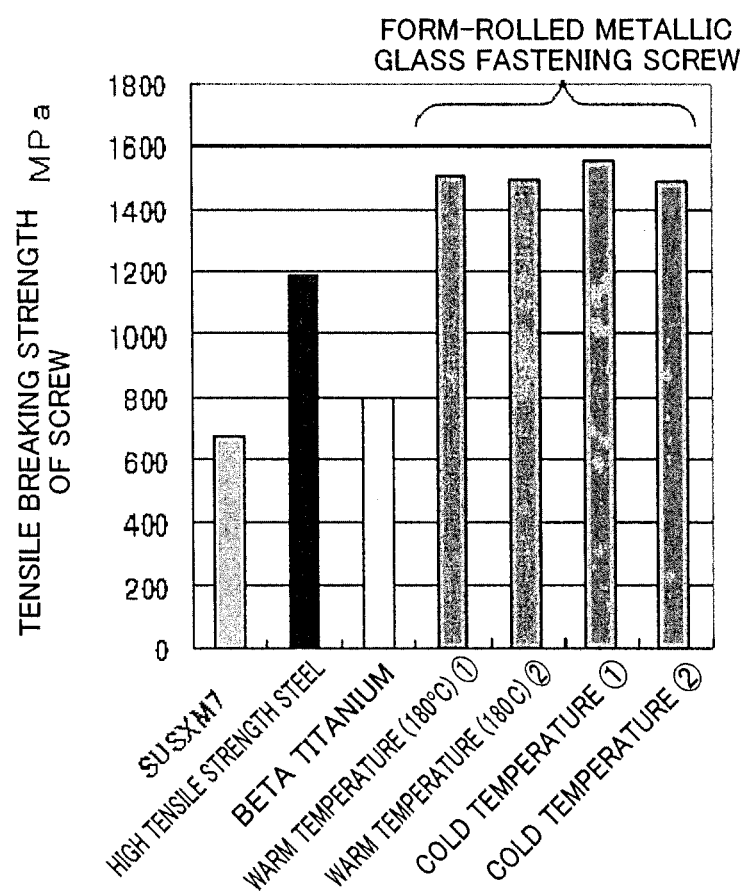
FIG. 13 shows comparison of screw tensile breaking strength.

FIG. 13 shows comparison of the tensile breaking strength between the screw of the present invention and other screws, all of which are M3 screws specified by JIS. The tensile breaking strength is compared with SUSXM7 (austenitic stainless screw), high tensile strength steel (high tensile strength bolt for mechanical fastening) and beta titanium (beta titanium screw with high strength) as the comparative materials. Two samples of the form-rolled metallic glass fastening screws of the present invention, form-rolled at warm temperature (180° C.) and at ambient temperature, respectively, are shown, and the strength for the both screws is about 1.3 times greater than that of the high tensile strength steel screw whose strength is the greatest among the screws to be compared. The M3 sized metallic glass fastening screw has the tensile breaking load almost corresponding to that of an M4 sized high tensile strength steel screw having the next larger size, according to the calculation.

The degree to which the tensile breaking strength of the screw is at variance is measured in the ten metallic glass fastening screws manufactured. The tensile breaking strength of the machined metallic glass fastening screws is at variance in the range of approximately 15% of the mean tensile breaking strength, but the form-rolled metallic glass fastening screw is at variance in the range of as small as 3%. This means that, in the form-rolled metallic glass fastening screw, the ductility at the screw groove is improved, the stress concentration is relaxed, and the breaking load is stabilized.

According to the metallic glass fastening screw form-rolled at the glass transition temperature or less, the tensile breaking strength of the screw has a greater value than those of other screws with high strength, its property of high elastic limit strain of the bulk metallic glass allows the axial force to stabilize, the contact area with the member to be fastened is increased and the frictional force is increased to allow the screw itself to have the property not susceptible to loosening, and the ductility on the screw surface is increased to relax the stress concentration of the screw groove and maintain the stable strength, so that the highly reliable fastening screw can be provided.

INDUSTRIAL APPLICABILITY

The metallic glass fastening screws that are not susceptible to loosening are provided for lightweight members that are effective in reduction in CO2 emissions and energy saving, so as to widely contribute to the industry, The metallic glass fastening screws that are not susceptible to loosening are also provided for ceramic used as a part of a processing machine increasing in speed, in an wet area, and in corrosive environment, so as to widely contribute to the industry.

In the medical field, it is also possible to provide the metallic glass fastening screw used for the living bodies that is not susceptible to loosening by selecting the bulk metallic glass having biocompatibility (Ti-base, Pd-base, Zr—Pd-base and the like) and by selecting the bulk metallic glass whose modulus of elasticity closely resembles that of the member to be fastened, such as bones.

DESCRIPTION OF THE REFERENCE NUMERAL

1 Bulk metallic glass round bar
2 Machined intermediate-shaped product for screw
3 Material for casting
4 Cast intermediate-shaped product for screw
41 Screw head
42 Screw axis
5 Initial stage of form rolling
6 Middle stage of form rolling
7 Form-rolled screw
71 Form-rolled screw axis
8 Region with equivalent stress of 1800 MPa or more
9 Screw thread of triangular-threaded screw
10 Screw thread of square-threaded screw
11 Screw thread of trapezoidal-threaded screw
12 Region including slip band
13 Tensile plastic deformation region
14 Form-rolled screw thread
15 Slip band
P1 Rolling die movement side
P2 Rolling die fixture side
Q1 Outline with mean stress of 0 MPa
Q2 Outline with equivalent stress of 1800 MPa
Q3 Screw thread angle
R1 Tensile direction

The invention claimed is:

1. A metallic glass fastening screw comprising:
   a thread;
   a groove; and
   a plastic strain region disposed near a surface of the screw and being formed through molding amorphous bulk metallic glass by form rolling at a glass transition temperature or less of the bulk metallic glass, wherein
   the screw satisfies a relationship of $d>0.022\times D$ where a depth from a bottom of the groove to the plastic strain region is d, and an outside diameter of the screw is D.

2. The metallic glass fastening screw according to claim 1, wherein the screw is a triangular-threaded screw having a screw thread angle that is within a range of 40 to 70 degrees.

3. The metallic glass fastening screw according to claim 1, wherein the bulk metallic glass is used for biomaterials by including at least one of Ti-base, Pd-base and Zr-base.

4. The metallic glass fastening screw according to claim 1, wherein, the bulk metallic glass includes any one of Mg-base, Pt-base, Ti-base and Zr-base having a modulus of elasticity equal to or lower than a modulus of elasticity of a member to be fastened in order to avoid loosening due to permanent strain of the member to be fastened when fastening the screw to the member to be fastened, the member to be fastened having a low yield point and a low modulus of elasticity.

5. A manufacturing method of a metallic glass fastening screw according to claim 1, wherein the metallic glass fastening screw is molded by form rolling with mean stress of a plastically deformed region of bulk metallic glass being compressive stress or tensile stress of one-third or less of tensile breaking strength of the bulk metallic glass.

6. The metallic glass fastening screw according to claim 3, wherein, the bulk metallic glass includes any one of Mg-base, Pt-base, Ti-base and Zr-base having a modulus of elasticity equal to or lower than a modulus of elasticity of a member to be fastened in order to avoid loosening due to permanent strain of the member to be fastened when fastening the screw to the member to be fastened, the member to be fastened having a low yield point and a low modulus of elasticity.

7. A manufacturing method of a metallic glass fastening screw according to claim 3, wherein the metallic glass fastening screw is molded by form rolling with mean stress of a plastically deformed region of bulk metallic glass being compressive stress or tensile stress of one-third or less of tensile breaking strength of the bulk metallic glass.

8. A manufacturing method of a metallic glass fastening screw according to claim 4, wherein the metallic glass fastening screw is molded by form rolling with mean stress of a plastically deformed region of bulk metallic glass being compressive stress or tensile stress of one-third or less of tensile breaking strength of the bulk metallic glass.

9. A manufacturing method of a metallic glass fastening screw according to claim 6, wherein the metallic glass fastening screw is molded by form rolling with mean stress of a plastically deformed region of bulk metallic glass being compressive stress or tensile stress of one-third or less of tensile breaking strength of the bulk metallic glass.

10. The metallic glass fastening screw according to claim 4, wherein the permanent strain is depression.

11. The metallic glass fastening screw according to claim 6, wherein the permanent strain is depression.

* * * * *